(12) United States Patent
Velusamy et al.

(10) Patent No.: US 7,446,207 B2
(45) Date of Patent: Nov. 4, 2008

(54) ORGANIC DYE USED IN DYE-SENSITIZED SOLAR CELL

(75) Inventors: Marappan Velusamy, Taipei (TW); Koilpitchai R. Justin Thomas, Taipei (TW); Jiann T'suen Lin, Taipei (TW); Kuo-Chuan Ho, Taipei (TW); Ying-Chan Hsu, Taipei (TW)

(73) Assignee: CTCI Foundation, Taipei (TW)

( * ) Notice: Subject to any disclaimer, the term of this patent is extended or adjusted under 35 U.S.C. 154(b) by 80 days.

(21) Appl. No.: 11/236,935

(22) Filed: Sep. 27, 2005

(65) Prior Publication Data

US 2007/0073052 A1    Mar. 29, 2007

(51) Int. Cl.
C07D 285/14  (2006.01)
C07D 417/04  (2006.01)
C07D 409/04  (2006.01)

(52) U.S. Cl. .......................... 548/134; 549/59; 323/906
(58) Field of Classification Search ................ 548/134; 549/59; 323/906
See application file for complete search history.

(56) References Cited

OTHER PUBLICATIONS

"Photoelectric conversion properties of four novel carboxylated hemicyanine dyes on $TiO_2$ electrode" By Qiao-Hong Yao et al. / 2003 Journal of Materials Chemistry, vol. 13, No. 5 / pp. 1048-1053.

"Low-bandgap polymer photovoltaic cells" By J.K.J. Van Duren et al. / 2001 Synthetic Metals, vol. 121 / pp. 1587-1588.

"A low-cost, high-efficiency solar cell based on dye-sensitized colloidal $Tio_2$ films" By Brian O'Regan et al. / Oct. 24, 1991 Letters of Nature, vol. 353 / pp. 737-740.

"Organic Dyes Containing Thienylfluorene Conjugation for Solar Cells" By K. R. Justin Thomas et al. / Aug. 28, 2005 Chem Commun (Camb), Issue 32 / pp. 4098-4100.

"Organic Dyes Incorporating Low-Band-Gap Chromophores for Dye-Sensitized Solar Cells" By Marappan Velusamy et al. / Feb. 25, 2005 Organic Letters / pp. A-D.

"Organic Dyes Incorporating Low-Band-Gap Chromophores for Dye-Sensitized Solar Cells" By Marappan Velusamy et al. / Supporting Information http://pubs.acs.org/subscribe/journals/orlef7/suppinfo/ol050417f/ol050417fsi20050413_072501.pdf.

*Primary Examiner*—Rei-tsang Shiao
*Assistant Examiner*—Joseph R Kosack
(74) *Attorney, Agent, or Firm*—J.C. Patents (57) ABSTRACT

An organic dye used in a dye-sensitized solar cell is described, having general formula (1):

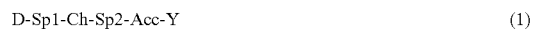

D-Sp1-Ch-Sp2-Acc-Y        (1)

wherein the groups D, Ch, Acc and Y are conjugate with each other, the group D is a donor group, the group Ch is a chromophore rendering low HOMO-LUMO gap or a polyaromatic chromophore, the group Acc is an acceptor group, the group Y is an anchoring group, and each of Sp1 and Sp2 represents a single bond or a spacer group allowing conjugation between the groups D and Ch or between the groups Ch and Acc.

1 Claim, 2 Drawing Sheets

ORGANIC DYE USED IN DYE-SENSITIZED SOLAR CELL

BACKGROUND OF THE INVENTION

1. Field of the Invention

The present invention relates to solar cell materials. More particularly, the present invention relates to an organic dye used in a dye-sensitized solar cell.

2. Description of the Related Art

The demand for energy conservation triggered the search for alternate renewable energy sources. A practical solution is the adoption of light-harvesting biological concepts. This biomimetic strategy has been recently translated into technological advances such as solar cells. Although silicon-based semiconductors dominated solar cell applications for decades, recent demonstration of dye-sensitized solar cells (DSSCs) based on nano-crystalline $TiO_2$ by Grätzel et al. (e.g., O'Regan, B.; Grätzel, M. Nature 1991, 353, 737) opened up the opportunity for organic and organometallic dyes in this area. A dye with excellent light-absorbing capability in the red and near-IR region, photostability, and redox stability is attractive for the functioning of DSSCs.

Coumarin-, indoline-, cyanine-, and hemicyanine based dyes have been used for the construction of DSSCs recently. However, the performances of DSSCs based on these large molecules are usually insufficient. On the other hand, though polymers based on small chromophoric groups like benzothiadiazole group have been employed in photovoltaic applications (e.g., van Duren, J. K. J.; Dhanabalan, A.; van Hal, P. A.; Janssen, R. A. J. Synth. Metals 2001, 121, 1587), small molecules containing such small chromophoric groups are never exploited for DSSCs.

SUMMARY OF THE INVENTION

Accordingly, this invention provides an organic dye used in a dye-sensitized solar cell, which is a small molecule containing a chromophore rendering a low HOMO-LUMO gap or a polyaromatic chromophore as a light-harvesting functional group.

The organic dye used in a dye-sensitized solar cell of this invention can be expressed by formula (1):

wherein the groups D, Ch, Acc and Y are conjugate with each other, the group D is a donor group, the group Ch is a chromophore rendering low HOMO-LUMO gap or a polyaromatic chromophore, the group Acc is an acceptor group, the group Y is an anchoring group, and each of Sp1 and Sp2 represents a single bond or a spacer group allowing conjugation between the groups D and Ch or between the groups Ch and Acc.

By including a chromophore rendering low HOMO-LUMO gap or a polyaromatic chromophore in the dye molecule, the performance of the present dye-sensitized solar cells can be improved dramatically when compared to that fabricated from certain cyanine and hemicyanine dyes.

It is to be understood that both the foregoing general description and the following detailed description are exemplary, and are intended to provide further explanation of the invention as claimed.

DESCRIPTION OF THE PREFERRED EMBODIMENTS

For the above organic dye expressed by formula (1), one example of the group Ch as a chromophore rendering low HOMO-LUMO gap is a benzo-[1,2,5]-thiadiazol-4,7-diyl or a benzo[1,2,5]selenadiazol-4,7-diyl group as expressed by:

wherein X represents sulfur or selenium. This type of heteroaromatic group has a low-lying LUMO and is electron-deficient.

One example of the group Ch as a polyaromatic chromophore is a (poly)thienylfluorene group including one to three thienylfluorene segments expressed by the following formula, or a derivative thereof obtained by substituting at least one H-atom thereon with a $C_1$-$C_4$ alkyl group.

For example, the two H-atoms on position 9 of the fluorene group can be substituted by ethyl groups to obtain the following group Ch. This type of light-harvesting segment may have higher absorption coefficient.

Another example of the group Ch as a chromophore rendering low HOMO-LUMO gap is a group expressed by the following formula, wherein X represents sulfur or selenium, and each of R1 and R2 represents hydrogen or a $C_1$-$C_4$ alkyl group. This type of heteroaromatic group has a low-lying LUMO, and is electron-deficient.

Another example of the group Ch as a polyaromatic chromophore is a carbazolyl group expressed by the following formula, or a derivative thereof obtained by substituting at least one H-atom thereon with a $C_1$-$C_4$ alkyl group, wherein R3 represents hydrogen or a $C_1$-$C_4$ alkyl group. This type of light-harvesting group may have higher extinction coefficient.

Another example of the group Ch as a polyaromatic chromophore is a fused thienylthiophene-based group expressed by the following formula, or a derivative thereof obtained by substituting at least one H-atom thereon with a $C_1$-$C_4$ alkyl group.

Another example of the group Ch as a polyaromatic chromophore is a thiophene-based group expressed by the following formula, or a derivative thereof obtained by substituting at least one H-atom thereon with a $C_1$-$C_4$ alkyl group, wherein n is equal to 2 or 3.

Another example of the group Ch as a polyaromatic chromophore is a group expressed by the following formula, or a derivative thereof obtained by substituting at least one H-atom thereon with a $C_1$-$C_4$ alkyl group.

The donor group D is, for example, a dialkylamino group or a diarylamino group, wherein the diarylamino group may contain at least one phenyl group, 1-naphthyl group, 9-anthracenyl group or 1-pyrenyl group. The acceptor group Acc is a 2-cyanoacryloxy or 2-cyanovinyl group, for example. The anchoring group Y may be a carboxylic acid group that can bind with $TiO_2$ to anchor the dye molecule. Preferably, the acceptor group Acc and the anchoring group Y in combination include a 2-cyanoacrylic acid group.

The symbol "Sp1" in formula (1) represents a single bond or a spacer group allowing conjugation between the groups D and Ch. When Sp1 represents a spacer group, examples of the spacer group include a p-phenylene group, a 2,5-thienylene group, the following group Sp1a and the following group Sp1b, wherein n is equal to 2 or 3.

(Sp1a)

p-phenylene:

(Sp1b)

2,5-thienylene:

The symbol "Sp2" in formula (1) represents a single bond or a spacer group allowing conjugation between the groups Ch and Acc. When Sp2 represents a spacer group, examples of the spacer group include a 2,5-thienylene group, a butadien-1,4-diyl group that may have a side chain on the 3-carbon atom forming a five- or six-member ring with the acceptor group Acc as in formula (10) mentioned later, a pyrimidine-2,5-diyl group, or a trans-vinylene-2,5-thiazolylene group shown below.

The preferred combinations of the above-mentioned groups D, Ch, Acc and Y, together with Sp1 and Sp2 each as a single bond or a spacer group, are expressed by the following formulae (2)-(13).

(2)

(3)

(4)

(5)

(6)

(7)

-continued

(8)

(9)

(10)

(11)

(12)

(13)

wherein Ar1 in formula (2) represents a p-phenylene group or a 2,5-thienylene group, Ar2 in formulae (3) and (10)-(13) represents 1-naphthyl, 9-anthracenyl or 1-pyrenyl, each of R1 and R2 in formula (9), R3 in formula (12) and R4 and R5 in formula (13) represents hydrogen or a $C_1$-$C_4$ alkyl group, X in formulae (2) and (4)-(9) represents sulfur or selenium, m in formula (3) is an integer of 1-3, n in formulae (5)-(7) and (10) is equal to 2 or 3, and each aprotic H-atom in each of formulae (2)-(13) can be substituted with a $C_1$-$C_4$ alkyl group.

Some examples among the above dyes are tested for their absorption/emission spectra and evaluated for their photovoltaic performances. These examples are given to further explain this invention, but are not intended to restrict the scope of the same.

EXAMPLE 1-4

In Examples 1-4, four dye compounds S1-S4 of general formula (2) are respectively synthesized and investigated.

Example 1: dye S1, X=S, Ar=$C_6H_4$ (p-phenylene)
Example 2: dye S2, X=Se, Ar=$C_6H_4$
Example 3: dye S3: X=S, Ar=$C_4H_2S$ (2,5-thienylene)
Example 4: dye S4: X=Se, Ar=$C_4H_2S$ In benzo(thia/selena)diazole-based fluorophores, the low-energy absorption is predominantly charge transfer in nature, and the same is true with the low-lying excited state also. This will ensure and enhance the possibility of charge separation and migration in such systems. The dyes were obtained in moderate yields in three steps as illustrated in Scheme 1.

Scheme 1:

In the first step, the donor is attached to the core either by Stille or Suzuki coupling reactions. These reactions produced the disubstituted side products as well. However monocapped compounds can be easily separated by column chromatography. In the next step, this bromo-exposed intermediate was reacted with (5-(1,3-dioxolan-2-yl)thiophen-2-yl)tributyl stannane under Stille coupling conditions, and subsequent cleavage of the 1,3-dioxalane protecting group in aqueous acetic acid produced the free aldehydes. These aldehydes, on reaction with cyanoacetic acid in the presence of ammonium acetate catalyst in acetic acid, produced the required dyes. The dyes are dark red or black in the solid state and freely dissolve in tetrahydrofuran (THF) to produce a red or violet solution.

TABLE 1

Electrooptical Parameters of the Dyes[a]

| Dye | $\lambda_{abs}$/nm ($\epsilon \times 10^{-3}$ $M^{-1}cm^{-1}$) | $E_{1/2}(ox)$ ($\Delta E_p$)/mV | $E_{1/2}(red)$ ($\Delta E_p$)/mV | HOMO, eV | LUMO, Ev | Band gap, eV |
|---|---|---|---|---|---|---|
| S1 | 491 (27.5), 388 (16.3), 309 (28.4) | 581 (91) | −1718 (90) | 5.381 | 3.260 | 2.121 |
| S2 | 502 (6.30), 351 (15.6) | 556 (77) | −1630 (96) | 5.356 | 3.338 | 2.018 |
| S3 | 541 (24.4), 398 (20.1), 312 (21.0) | 322 (85) | −1660 (106) | 5.122 | 3.256 | 1.866 |
| S4 | 544 (13.2), 363 (26.5) | 263 (107) | −1556 (138) | 5.063 | 3.290 | 1.773 |

[a] Absorption and electrochemical data were collected in tetrahydrofuran solutions. Scan rate, 100 mV/sec; electrolyte, $(n-C_4H_9)_4NPF_6$; $\Delta E_p$ is the separation between the anodic and cathodic peaks. Potentials are quoted with reference to the internal ferrocene standard ($E_{1/2}$ = +265 mV vs. Ag/AgNO$_3$).

Figure 1:
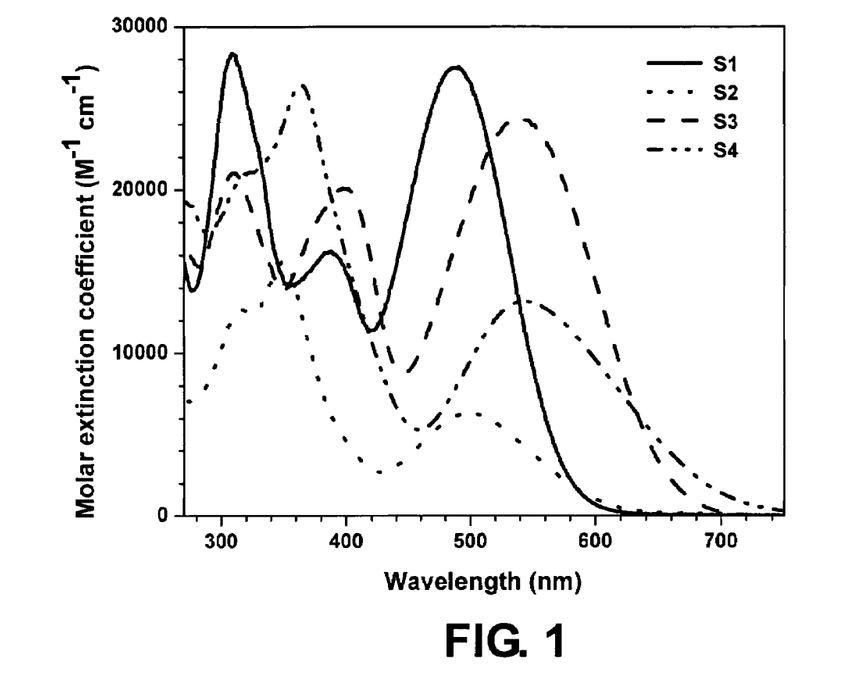
FIG. 1 shows the absorption spectra of the dyes S1-S4 recorded in THF in Examples 1-4 of this invention.

The absorption spectra recorded for the THF solution of the dyes are displayed in FIG. 1. All the dyes exhibit three transitions and cover a broad range (250-700 nm) of spectra (FIG. 1 and Table 1). For the similar structural architecture, the benzoselenadiazole derivatives (S2 and S4) display red-shifted absorption when compared to the benzothiadiazole analogues (S1 and S3). However, the benzoselena-diazole derivatives possess less optical density for the CT transition. Another effect due to the linking aromatic segment was also noticed, i.e., the thiophene-linked compounds (S3 and S4) show bathochromic shift for the charge-transfer band when compared to the phenylene-linked derivatives (S1 and S2).

The drop in the extinction coefficient of the CT absorption in the benzoselena-diazole derivatives (S2 and S4) is more pronounced for the phenylene-conjugated derivative S2 (4.37 times when compared to S1) than for the thiophene-linked analogue S4 (1.85 times when compared to S3). These observations are attributed to the larger size and smaller electronegativity of Se when compared to S. These factors will lead to less electron density on Se and thus diminished aromaticity for benzoselenadiazole when compared to benzothiadiazole. Similarly, the increased donor property and coplanar arrangement of thiophene with the core substantially compensate the drop in transition probability for S4.

The dyes are redox stable, exhibiting both quasi-reversible oxidation and reduction couples. Dyes with good redox stability are required for sustaining dye-sensitized solar cells. Benzothiadiazole-based derivatives containing triarylamines have been reported to undergo facile oxidation and reduction. Similarly, in the current derivatives, the oxidation and reduction also originate from the amino and benzothiadiazole/benzoselenadiazole functionality, respectively. Thiophene linker slightly influences the redox potentials. Benzoselenadiazole derivatives display negative shift in oxidation potentials and positive shift in the reduction potentials when compared to the benzothiadiazole derivatives. This results in a substantial reduction in the band gap for the benzoselenadiazole derivatives when compared to the benzothiadiazole analogues (see Table 1).

Figure 2:
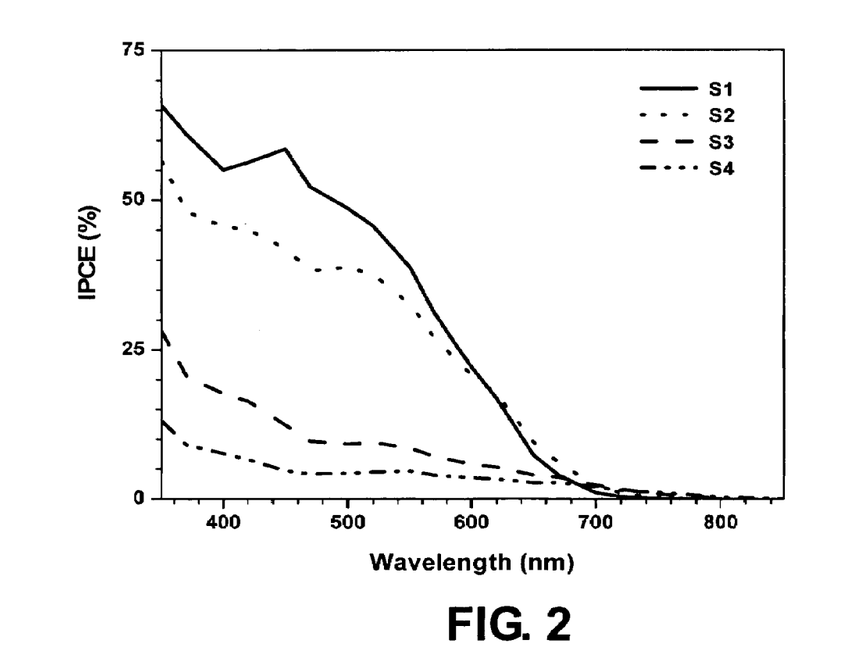
FIG. 2 shows the action spectra for the dyes. S1-S4 in Examples 1-4.

The dye-sensitized solar cells were constructed using these dyes as a sensitizer for nano-crystalline anatase $TiO_2$. Typical solar cells, with an effective area of 0.25 cm², were fabricated with 0.05M $I_2$/0.5M LiI/0.5M tert-butyl pyridine in acetonitrile solution as an electrolyte. The device performance statistics under AM 1.5 illumination are collected in Table 2. The incident to photon conversion efficiency data at each wavelength are plotted for S1-S4 in FIG. 2. From the data, it is evident that dyes S1 and S2 exhibit impressive photovoltaic performances. The open-circuit photovoltage and overall yield for the four dyes lie in the order S1>S2>S3~S4.

TABLE 2

Performance Parameters of DSSCs Constructed Using the Dyes[a]

| Dye | $V_{OC}$, mV | $J_{SC}$, mA cm$^{-2}$ | ff | η, % |
|---|---|---|---|---|
| S1 | 546 | 10.44 | 0.66 | 3.77 |
| S2 | 524 | 8.35 | 0.67 | 2.91 |
| S3 | 517 | 3.21 | 0.69 | 1.15 |
| S4 | 474 | 3.57 | 0.66 | 1.11 |
| N3 | 708 | 11.28 | 0.66 | 5.30 |

[a]Experiments were conducted using $TiO_2$ photoelectrodes with approximately 14 μm thickness and 0.25 cm² working area on the FTO (7 Ω/sq) substrates.

The difference in performance between the phenylene-conjugated derivatives (S1 and S2) and the thiophene-linked analogues (S3 and S4) probably stems from the difference in the coplanarity of the aromatic segment that bridges the donor and acceptor units. Molecular modeling (SPARTAN, PM3) studies reveal that the phenlylene derivatives (S1 and S2) possess a twisted non-planar geometry, which will decelerate the recombination of charges in the charge-separated state. Additionally, in the phenylene derivatives (S1 and S2), the reorganization energy required for the decoupled twisted state may be more favorable when compared to the thiophene analogues (S3 and S4).

Energy-minimized structure of S1:

Energy-minimized structure of S3:

Accordingly, the above-mentioned benzo(thia/selena)diazole-based dyes can be successfully adsorbed on nano-crystalline anatase $TiO_2$ particles to form efficient dye sensitized solar cells. The performance of these small-molecule-based, dye-sensitized solar cells is better than that fabricated from certain cyanine and hemicyanine dyes (e.g., Yao, Q.-H.; Meng, F.-S.; Li, F.-Y.; Tian, H.; Huang, C.-H. *J. Mater. Chem.* 2003, 13, 1048). The approach is unique in that it uses an easily polarizable and electron-deficient bridge between the push-pull chromophores, leading to push-pull-pull architecture that is different from that used previously, which contains a donor and an acceptor bridged through an aromatic or aliphatic linker.

EXAMPLES 5-9

In Examples 5-9, five dye compounds 9-13 of general formula (3) are respectively synthesized and investigated. The thienylfluorene group in formula (3) is an electron-rich group (3)

Example 5: dye 9, n=1; Ar=1-naphthyl
Example 6: dye 10, n=1; Ar=9-anthracenyl
Example 7: dye 11, n=1; Ar=1-pyrenyl
Example 8: dye 12, n=2; Ar=1-naphthyl
Example 9: dye 13, n=3; Ar=1-naphthyl The dyes were constructed by an iterative synthetic protocol illustrated in Scheme 2.

Scheme 2:

9: Ar = 1-naphthyl
10: Ar = 9-anthracenyl
11: Ar = 1-pyrenyl

6: Ar = 1-naphthyl
7: Ar = 9-anthracenyl
8: Ar = 1-pyrenyl

3: Ar = 1-naphthyl
4: Ar = 9-anthracenyl
5: Ar = 1-pyrenyl

Figure 3:
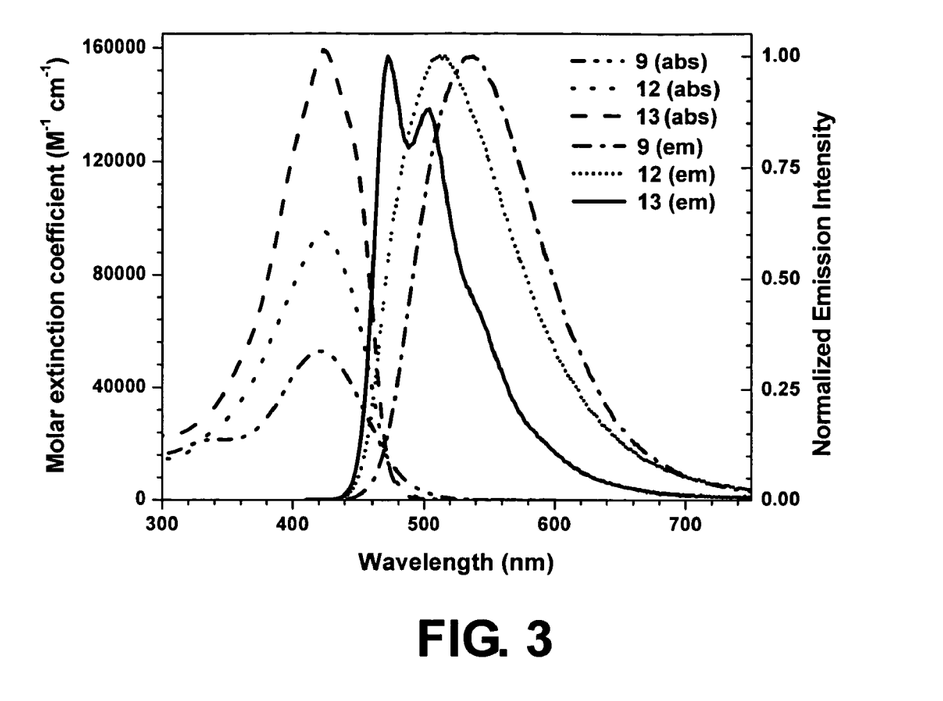
FIG. 3 shows the absorption and emission spectra of the dyes 9, 12 and 13 recorded in THF in Examples 5-9 of this invention.

From the known compound, 2-(7-bromo-9,9-diethyl-9H-fluoren-2-yl)thiophene (2) diarylamine substituted fluorenylthiophene derivatives (3-5) were obtained by the C—N coupling reactions involving Hartwig's catalyst and the corresponding diarylamine. These thiophene derivatives were converted into their corresponding thiophenealdehydes (6-8) by lithiation with n-butyl lithium and subsequent quenching with dimethylformamide. Later the aldehydes 6-8 were converted to the dyes 9-11 by reaction with cyanoacetic acid in refluxing acetic acid in the presence of ammonium acetate. In the another step, the stannylene precursor of the derivative 3 prepared by treating the lithium derivative of the derivative 3 with tributyltin chloride in THF was used in the Stille reaction with the compound 2 to produce the bis(thienylfluorene) conjugated analog of the derivative 3. This was then converted to the aldehyde which produced the dye 12 on treatment with cyanoacetic acid. One more similar iterative sequence starting with the bis(thienylfluorene) conjugated analog of the derivative 3 was executed to obtain the third generation dye 13. The dyes are red colored and soluble in THF.

band probably the representing the superposition of π-π* and charge transfer transitions. The optical density of this band increases rapidly on extending the conjugation by introducing the additional thienylfluorene segments (FIG. 3). These compounds are the first examples of DSSC active dyes to date to display larger absorption coefficients. Interestingly, the interaction between the donor and acceptor gets minimized on increasing the conjugation length of the bridge. This is reflected in the emission band position of the dyes 9, 12 and 13. Consequently, this slightly deters the magnitude of charge separation for elongated derivatives 12 and 13.

The dyes can be reversibly oxidized at moderately high oxidation potentials. The oxidation potentials are more positive than the ferrocene/ferrocenium and $I^-/I_3^-$ redox couples. Oxidation higher than iodine couple is necessary to forbid the backward electron transfer to electrolyte solution and ensure forward electron injection into the $TiO_2$ layer in the DSSC setup. The reversibility of the oxidation couple will be beneficial for the stability of the DSSCs on long run.

TABLE 3

Optical, redox and DSSCs performance parameters of the dyes

| Dye | $\lambda_{abs}$, nm ($\epsilon$, $M^{-1}cm^{-1}$) | $\lambda_{em}$, nm ($\Phi_F$, %) | $E_{ox}$ ($\Delta E_p$), mV | $V_{OC}$, V | $J_{SC}$, mA/cm$^2$ | ff | η (%) |
|---|---|---|---|---|---|---|---|
| 9 | 421 (52,900) | 538 (0.28) | 509 (82) | 0.65 | 12.47 | 0.65 | 5.23 |
| 10 | 421 (46,300) | 536 (0.19) | 451 (109) | 0.57 | 7.59 | 0.67 | 2.86 |
| 11 | 425 (54,500) | 537 (0.33) | 462 (66) | 0.60 | 8.38 | 0.67 | 3.35 |
| 12 | 423 (95,500) | 512 (0.26) | 447 (59), 613 (61) | 0.61 | 9.83 | 0.65 | 3.89 |
| 13 | 423 (1,59,200) | 472, 504 (0.37) | 437 (65), 569 (70) | 0.61 | 9.81 | 0.64 | 3.80 |
| N3 | | | | 0.62 | 13.98 | 0.63 | 5.50 |

Figure 4:
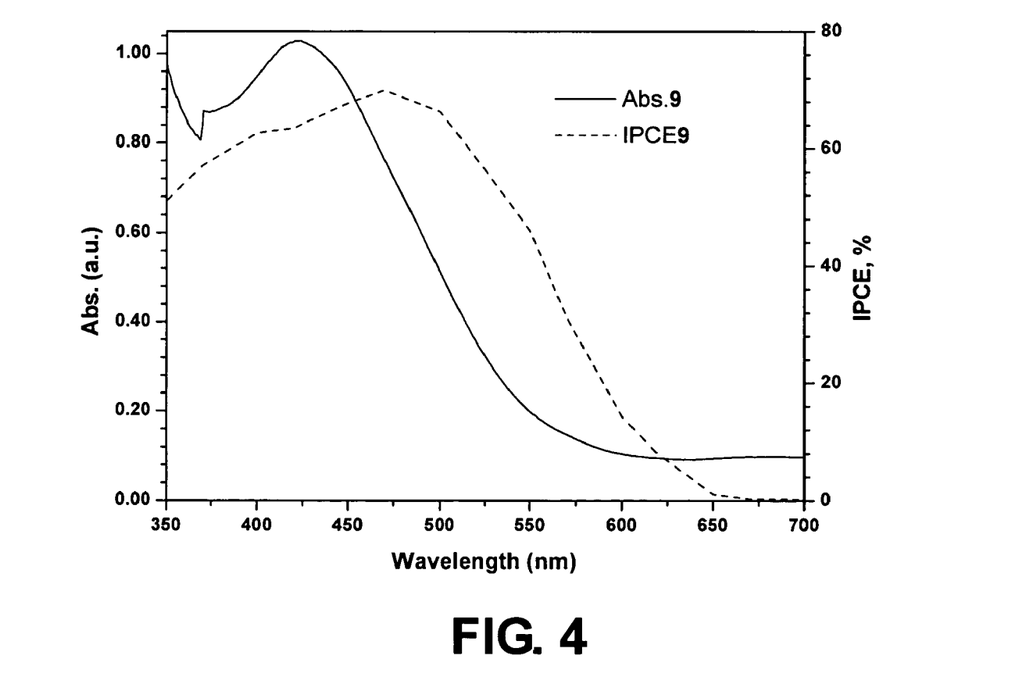
FIG. 4 shows the absorption spectra of the dye 9 that is adsorbed on nano-crystalline $TiO_2$ and the action spectra for the DSSC constructed using the dye 9.

The absorption and emission spectra of the dyes recorded in THF solution are displayed in FIG. 3 and the data are collected in Table 3. All the dyes exhibit a single prominent The DSSCs fabricated, with effective area 0.25 cm$^2$, using these dyes as light harvesting sensitizers, nano-crystalline anatase $TiO_2$ particles, and the electrolyte composed of 0.05M I$_2$/0.5M LiI/0.5M tert-butylpyridine in acetonitrile solution showed impressive photon-to-electron conversion. The device performance statistics under AM 1.5 illumination are listed in Table 3. Particularly the device manufactured with the dye 9 performed closely as the standard ruthenium dye N3. The action spectra and absorption spectra of the dye 9 adsorbed on TiO$_2$ is presented in FIG. 4. We believe that the dark current minimization due to difficulty in the oxidation of dye 9 accounts for the difference in performance among the dyes. Incidentally, the oxidation potential of 9 is slightly higher than other dyes. Additionally, energy minimized ground and excited state structures of the dye 9 and ground state structure of the dye 12 possesses twisted thienyl and fluorenyl segments. On the contrary, the excited state structure of the dye 12 is predominantly coplanar in nature. A coplanar excited state structure may enhance the effective conjugation and facilitate the charge recombination processes. Consequently, the excited state dipole moment of 9 is double than that of the ground state geometry. However the conjugated dyes (12 and 13) do not show any change in the ground and excited state dipole moments.

Accordingly, Examples 5-9 investigate a series of dyes featuring thienylfluorene conjugation, diarylamine donors and 2-cyanoacrylic acid acceptors. Despite the lower wavelength absorption, the DSSC performance achieved for a dye nearing to that of N3 is intriguing.

In summary, this invention provides a new class of dyes featuring donor-acceptor architecture that incorporates a chromophore rendering low HOMO-LUMO gap or a polyaromatic chromophore. They can be successfully adsorbed on nano-crystalline anatase TiO$_2$ particles to make efficient DSSCs. The performance of these small-molecule-based, dye-sensitized solar cells is better than that fabricated from certain cyanine and hemicyanine dyes. This design opens up the possibility of preparing new dye molecules for DSSCs utilizing low-band-gap building blocks.

It will be apparent to those skilled in the art that various modifications and variations can be made to this invention without departing from the scope or spirit of this invention. Hence, it is intended that this invention covers its modifications and variations provided they fall within the scopes of the claims and their equivalents.

What is claimed is:

1. An organic dye used in a dye-sensitized solar cell, expressed by the following formula:

wherein X represents sulfur or selenium, and Ar represents a p-phenylene group or a 2,5-thienylene group.

* * * * *